United States Patent [19]
Patel et al.

[11] Patent Number: 5,484,802
[45] Date of Patent: Jan. 16, 1996

[54] FUNGICIDAL ALPHA-(DIOXOIMIDAZOLIDINE)ACETANILIDE COMPOUNDS

[76] Inventors: Bomi P. Patel, 1407 Orchard Way, Rosemont, Pa. 19010; Jerome M. Lavanish, 293 Forrest Rd., Yardley, Pa. 19067

[21] Appl. No.: 412,671

[22] Filed: Mar. 29, 1995

[51] Int. Cl.$^6$ .......................... A01N 43/50; C07D 233/02
[52] U.S. Cl. ........................................ 514/390; 548/317.5
[58] Field of Search ...................... 548/317.5; 514/390

[56] References Cited

U.S. PATENT DOCUMENTS

| | | | |
|---|---|---|---|
| 4,428,948 | 1/1984 | Miller et al. | 548/317.5 |
| 5,204,366 | 4/1993 | Lavanish et al. | 514/424 |

OTHER PUBLICATIONS

F. Kurzer, Organic Synthesis 31, pp. 52–54 (1951).

D. Ben–Ishai et al, J. Heterocyclic Chem, 7(6), pp. 1289–1293 (1970).

S. Tokita et al., Synthesis Communications, pp. 270–271 (1983).

*Primary Examiner*—Patricia L. Morris
*Attorney, Agent, or Firm*—Gregory M. Hill

[57] ABSTRACT

There are provided α-(dioxoimidazolidine)acetanilide compounds which are effective for the control of phytopathogenic fungi, the control and prevention of disease caused thereby and the protection of crops therefrom. Further provided are fungicidal methods and compositions comprising said compounds.

20 Claims, No Drawings

FUNGICIDAL ALPHA-(DIOXOIMIDAZOLIDINE)ACETANILIDE COMPOUNDS

BACKGROUND OF THE INVENTION

Food production relies upon a variety of agricultural technologies to ensure the growing population's dietary needs remain affordable, nutritious and readily available on grocery store shelves. Fungicides are one of these agricultural technologies which are available to the world community. Fungicides are agrochemical compounds which shield crops and foods from fungus and fungal diseases. Crops and food are constantly threatened by a variety of fungal organisms, which, if left uncontrolled, can cause ruined crops and devastated harvests.

Therefore, it is an object of this invention to provide α-(dioxoimidazolidine)acetanilide compounds that are highly effective for controlling phytopathogenic fungi and controlling or preventing disease caused thereby.

It is another object of this invention to provide methods and compositions for the protection of important agronomic crops from the damage and loss caused by fungal infection and disease.

Further objects and features of the invention will become apparent from the detailed description provided herein below.

SUMMARY OF THE INVENTION

The present invention provides α-(dioxoimidazolidine)acetanilide compounds of formula I

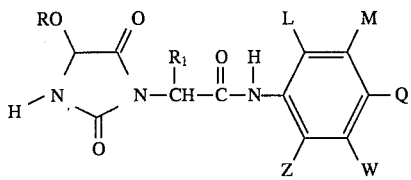

wherein

R is hydrogen, $C_1$–$C_4$haloalkyl or benzyl;

$R_1$ is hydrogen, $C_1$–$C_8$alkyl, $C_3$–$C_6$cycloalkyl, phenyl, benzyl or phenethyl;

L, M, Q, W and Z are each independently hydrogen, $C_1$–$C_6$ alkyl, $C_1$–$C_4$alkoxyalkyl, $C_1$–$C_6$haloalkyl, $C_1$–$C_4$alkoxy, halogen, $NO_2$, CN, $CO_2R_3$, phenyl or phenoxy with the proviso that no more than 3 of L, M, Q, W and Z may be phenyl or phenoxy;

$R_3$ is $C_1$–$C_4$ alkyl; and when $R_1$ is a substituent other than hydrogen, the optical isomers thereof.

The present invention also provides a method for the control, prevention or amelioration of disease caused by a phytopathic fungus which comprises contacting said fungus with a fungicidally effective amount of a compound of formula I.

Compositions useful as fungicidal agents and crop protection methods are also provided.

DETAILED DESCRIPTION OF THE INVENTION

Huge economic losses have resulted from the devastation and damage of important agronomic and horticultural crops caused by fungal infection and infestation. Pest management strategies, field resistance, and virulent strains have all contributed to agriculturalists' concerns for combatting phytopathogenic fungal disease.

It has now been found that α-(dioxoimidazolidine)acetanilide compounds of formula I are highly effective fungicidal agents and are particularly effective for controlling mildew diseases such as grape downey mildew and blight diseases such as tomato late blight.

A preferred group of formula I α-(dioxoimidazolidine)acetanilide compounds described above are those wherein R is $C_1$–$C_8$alkyl $C_1$–$C_8$haloalkyl or benzyl;

$R_1$ is hydrogen, $C_1$–$C_8$alkyl, benzyl or phenethyl; and

L, M, Q, W and Z are each independently hydrogen, $C_1$–$C_6$ alkyl, $C_1$–$C_4$alkoxy, halogen, phenyl or phenoxy with the proviso that no more than 3 of L, M, Q, W and Z may be phenyl or phenoxy.

A more preferred group of formula I compounds are those wherein

R is $C_1$–$C_8$alkyl;

$R_1$ is hydrogen, $C_1$–$C_6$alkyl, benzyl or phenethyl; and

L, M, Q, W and Z are each independently hydrogen, $C_1$–$C_6$ alkyl, $C_1$–$C_4$alkoxy, or halogen.

The term halogen designates F, Cl, Br or I. The term haloalkyl designates an alkyl group $C_nH_{2n+1}$ containing from one to 2n+1 halogen atoms.

The formula I α-(dioxoimidazolidine)acetanilide compound may be prepared by reacting an amino acid having formula II

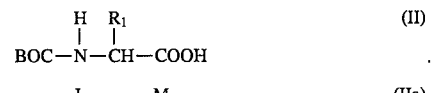

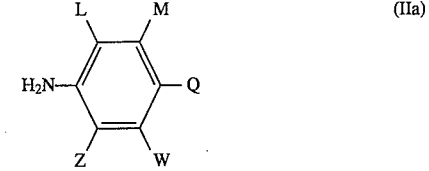

wherein $R_1$ is as described above for formula I and BOC is the protecting group tert-butoxycarbonyl, with at least one molar equivalent of a formula IIa aniline wherein L, M, Q, W, and Z are as described above for formula I and at least one molar equivalent of a coupling agent in the presence of a solvent to form the protected amine anilide of formula III.

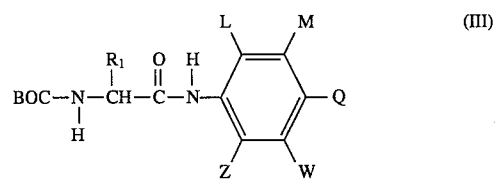

The protecting group may be removed in the presence of one molar equivalent of an aqueous acid to yield the unprotected amine anilide of formula IV.

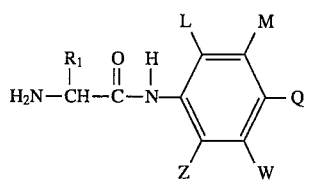
(IV)

The formula IV amine anilide may be reacted with one molar equivalent of urea in the presence of an aqueous and/or organic acid to form the urea anilide of formula V.

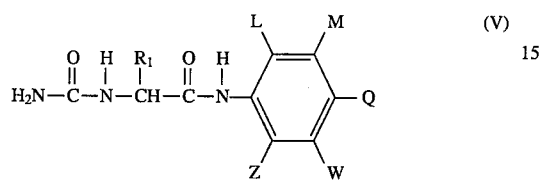
(V)

The urea anilide of formula V may be reacted with one molar equivalent of butyl glyoxalate to form the intermediate compound of formula VI.

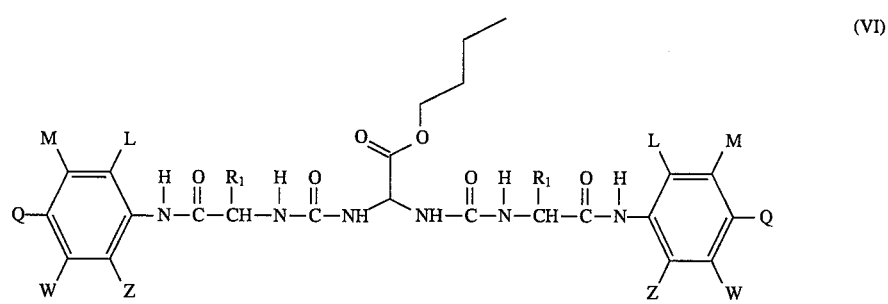
(VI)

The formula VI intermediate may be reacted with at least one molar equivalent of triethylamine to form the α-(dioxoimidazolidine)acetanilide of formula VII.

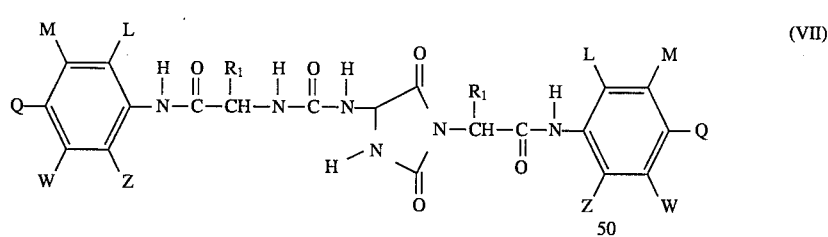
(VII)

The formula VII α-(dioxoimidazolidine)acetanilide may be reacted with at least one molar equivalent of aqueous acid in alcohol to form the desired α-(dioxoimidazolidine)acetanilide product of formula I. The above reaction sequence is summarized below in flow diagram I.

Flow Diagram I

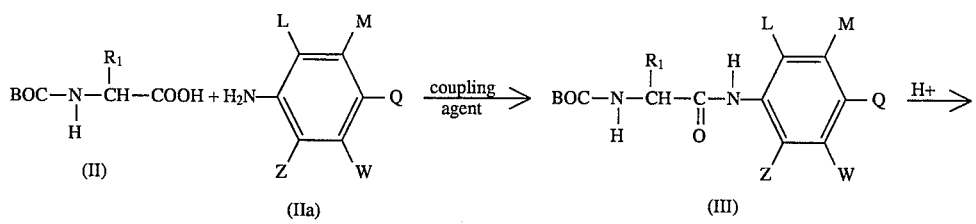

-continued
Flow Diagram I

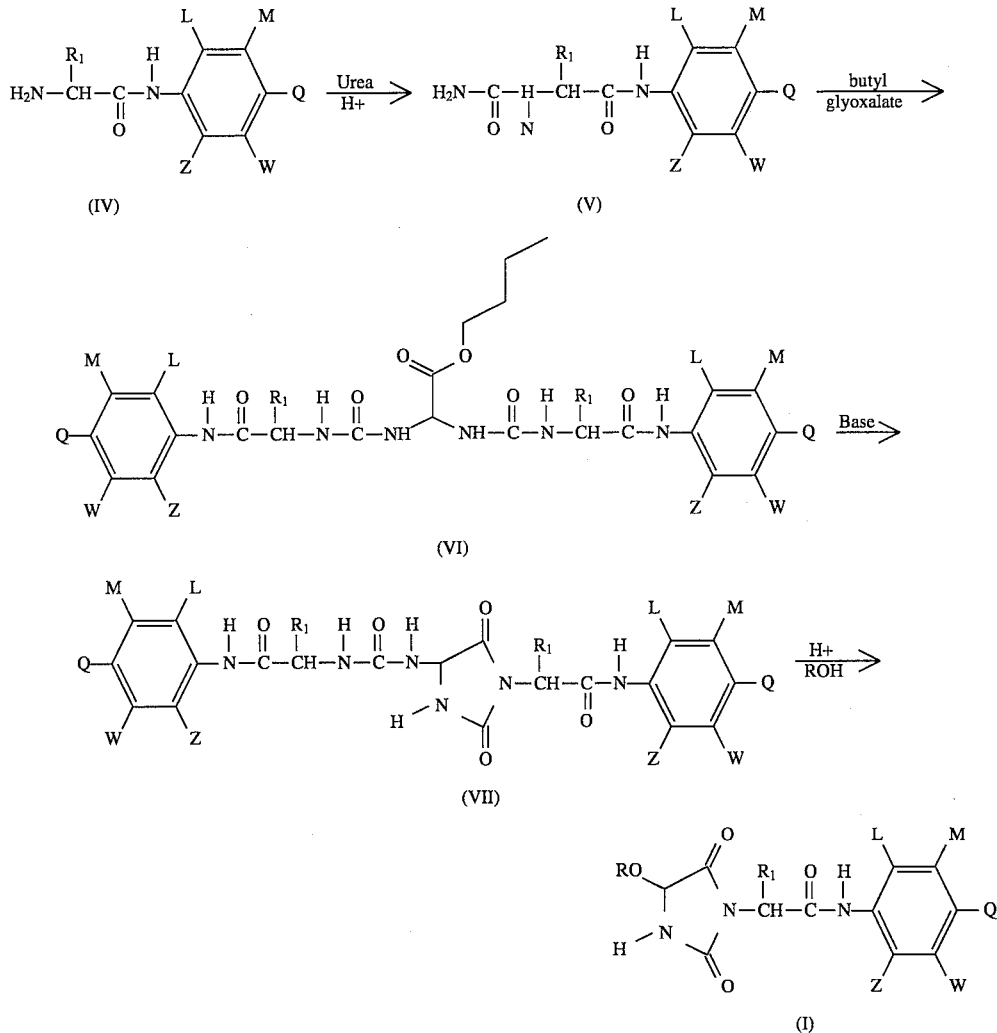

Bases suitable for use in the above reaction sequence include organic bases such as trialkylamine, pyridine, dimethylaminopyridine and the like.

The formula I compound of the present invention is effective for controlling or preventing the growth of phytopathogenic fungi, particularly members of the oomycota such as *Plasmopara viticola, Phytophthora infestans* and the like. Phytopathogenic fungal growth may be effectively controlled or prevented in the presence of growing or harvested crops when the inventive formula I compound is applied to the locus of said crops or the crop plant, seed, or tuber at a fungicidally effective rate. This rate will vary according to the virulence of the pathogen, the degree of infestation, weather conditions, soil conditions, crop species, mode of application, application time and the like. The Formula I compound may be applied to infected plants to control or ameliorate infection. Further, said compound may also be applied to healthy plants or seed or to the soil in which the plant is to be grown in order to prevent fungal infestation and infection.

In actual practice, the formula I compound is applied in the form of a liquid formulation, preferably as an aqueous spray, or dust, or granular formulation. Solutions or suspensions containing about 20 ppm to 1,000 ppm, preferably about 50 ppm to 500 ppm, of the formula I compound is generally effective.

In general, the α-(dioxoimidazolidine)acetanilide compound of the invention may be formulated as an emulsifiable concentrate, flowable concentrate, microemulsion, wettable powder and the like, which can be diluted with water or other suitable polar solvent and then applied as a dilute spray. Said compound may also be formulated as a dry compacted granule, granular formulation, dust, dust concentrate, suspension concentrate, and the like. Any composition suitable for use as a seed, soil, water and/or foliage application is suitable. Such compositions include the formula I compound of the invention admixed with an agriculturally acceptable solid or liquid diluent.

For example, wettable powders, dusts, and dust concentrate formulations can be prepared by grinding and blending together about 25–85% by weight of a formula I compound, about 75–15% by weight of a solid diluent such as bentonite, diatomaceous earth, kaolin, attapulgite, and the like, about 1–5% by weight of a dispersing agent such as sodium lignosulfonate, and about 1–5% by weight of a nonionic surfactant, such as octylphenoxy polyethoxy ethanol, nonylphenoxy polyethoxy ethanol and the like.

A typical emulsifiable concentrate can be prepared by dissolving about 15% to 70% by weight of the active ingredient in about 85% to 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

It is contemplated the α-(dioxoimidazolidine)acetanilide compound of the present invention may be applied alone or in combination with one or more other fungicidal agents, such application may be made either by the combination of the fungicidal compounds, or their formulations, in a common container prior to use, or by sequential application of the active fungicidal compounds, or their formulations, to the host crop or its environs. Among the fungicidal agents suitable for combination with the formula I compound of the invention are the following: 4,6-dinitro-o-cresol, benalaxyl, benomyl, captafol, captan, carbendazim, chlorothalonil, copper, cymoxanil, dichlobutrazole, dichlofluanid, diethofencarb, difenconazole, dimethomorph, diniconazole, dinocap, dithianon, fenarimol, fentin acetate, ferbam, flusilazole, folpet, fosetyl, hexaconazole, imazalil, iprodione, mancopper mancozeb, maneb, mepronil, mercuric oxide, metalaxyl, metiram, myclobutanil, nuarimol, ofurace, oxadixyl, penconazole, pencyuron, phosphorous acid, procymidone, propineb, pyrifenox, quintozene, sodium arsenite, sulphur, thiabendazole, thiophanate methyl, thiram, tolclophos-methyl, triadimefon, triadimenol, triforine, vinclozolin, zineb, ziram, and the like.

For a more clear understanding of the invention, the following specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims. The terms HNMR, CIMS and IR as used in the hereinbelow designate proton nuclear magnetic resonance, mass spectrum and Infrared, respectively.

EXAMPLE 1

PREPARATION OF N-BOC-2-AMINO-4'-CHLORO-3-METHYL L-BUTYRANLILDE

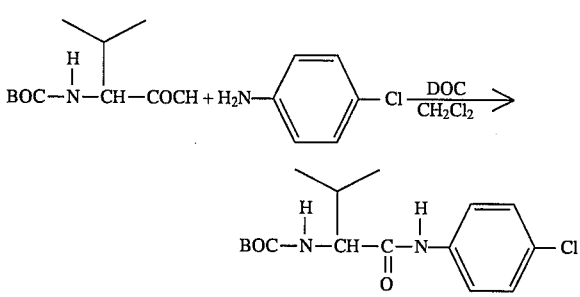

A solution of N-BOC-L-valine (20 g) in methylene chloride at 0° C. is treated with dicyclohexylcarbodiimide (19.6 g), stirred for 5 minutes, treated with p-chloroaniline (10.5 g), stirred for 3 hours and filtered. The filtrate is washed with 10% aqueous hydrochloric acid and concentrated in vacuo to give the title product as a white solid (22 g), identified by HNMR analysis.

EXAMPLE 2

PREPARATION OF 2-AMINO-4'-CHLORO-3-METHYL L-BUTYRANILIDE

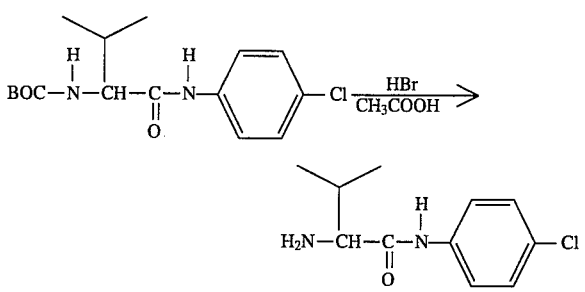

A solution of N-BOC-2-amino-4'-chloro-3-methyl L-butyranilide (10 g) in a mixture of hydrobromic acid and acetic acid is stirred for 5 hours, concentrated in vacuo and extracted with ether. The aqueous layer is basified with sodium hydroxide and extracted with methylene chloride. The methylene chloride extract is concentrated in vacuo to give the title product as a white solid (5.8 g), identified by HNMR analysis.

EXAMPLE 3

PREPARATION OF 1-{1-[(P-CHLOROPHENYL)CARBAMOYL]-2-METHYLPROPYL}UREA

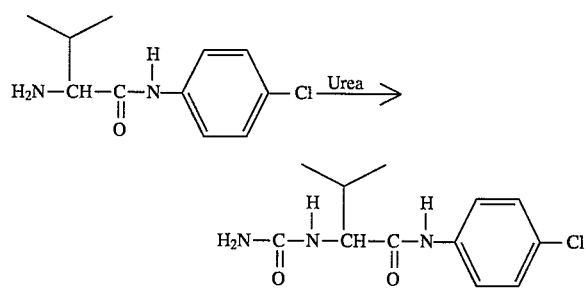

A solution of 2-amino-4'-chloro-3-methyl L-butyranilide in ether is treated with 1N hydrochloric acid in ether until precipitation is complete. The resultant mixture is filtered. The filter cake (6.2 g) is dissolved in water, treated with 0.2 ml of 37% aqueous hydrochloric acid, 0.2 ml of aqueous acetic acid and urea (5.8 g), refluxed for 6 hours, cooled and filtered to give the title product as a white solid (2.2 g, mp 238°–240° C.), identified by HNMR, CIMS and IR analyses.

EXAMPLE 4

PREPARATION OF DL, DL-BIS[3-{1-[(P-CHLOROPHENYL)CARBAMOYL]-2-METHYLPROPYL}UREIDO}ACETIC ACID, BUTYL ESTER

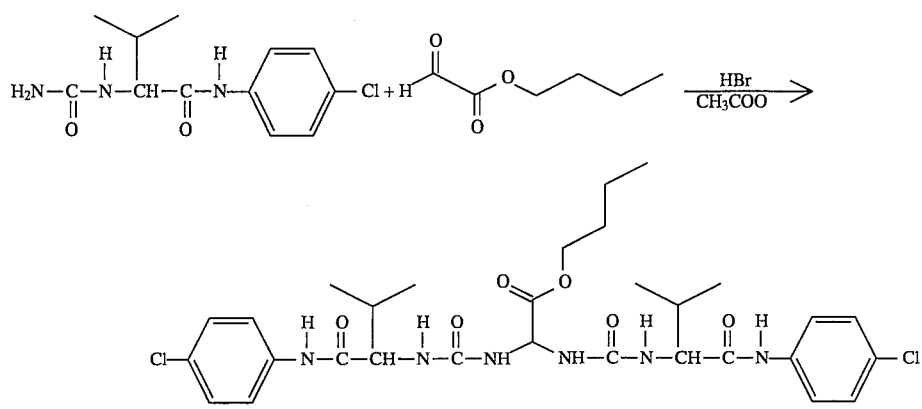

A solution of 1-{1-[(p-chlorophenyl)carbamoyl]-2-methylpropyl}urea (2.8 g) in a mixture of glacial acetic acid and 0.5 ml of 1M hydrobromic acid in acetic acid is treated with butylglyoxalate(0.8 g), stirred for 72.hours and filtered to give the title product as a white solid (2.9 g, mp 219°–221° C.), identified by HNMR, CIMS and IR analyses.

EXAMPLE 5

PREPARATION OF DL,DL-1-[(P-CHLOROPHENYL)CARNAMOYL]-2-METHYLPROPYL} -3-{1-(P-CHLOROPHENYL)CARBAMOYL]-2-METHYLPROPYL} -2,5-DIOXO-4-IMIDAZOLIDINYLUREA product as a pale yellow oil (1.2 g), identified by HNMR, CIMS and IR analyses.

EXAMPLE 6

PREPARATION OF DL-4'-CHLORO-a-ISOPROPYL-2,5-DIOXO-4-METHOXY- 1-IMIDAZOLIDINEACETANILDE

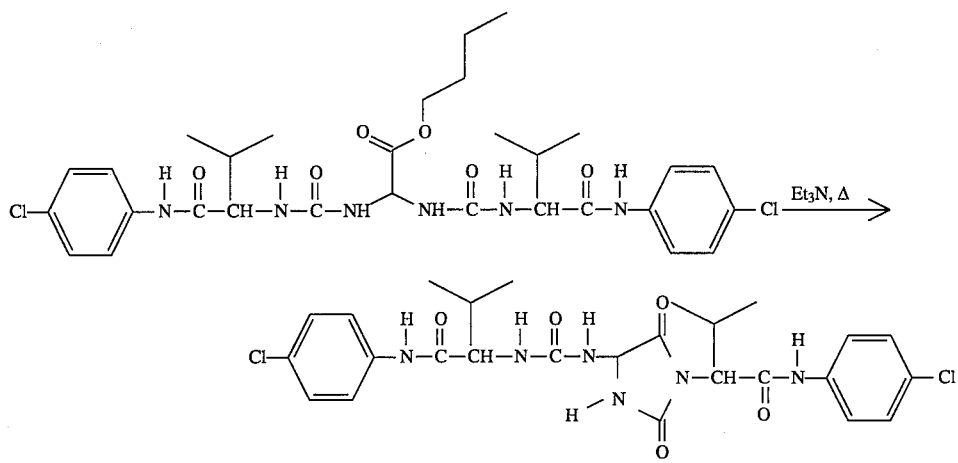

A suspension of DL, DL-bis-[3-{1-[(p-chlorophenyl)carbamoyl]-2-methylpropyl}ureido}acetic acid, butyl ester (1.5 g) in methanol is treated with 1 ml of triethylamine, refluxed for 8 hours, cooled and concentrated in vacuo to give the title

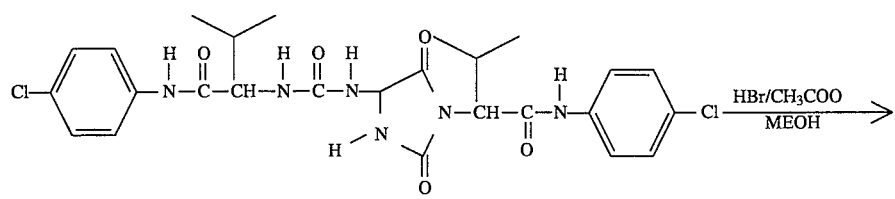

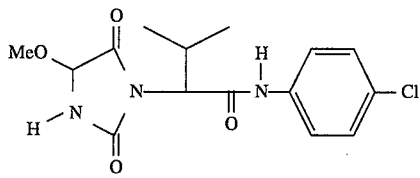

A solution of DL,DL-1-[(1-[(p-chlorophenyl)carbamoyl]-2-methylpropyl}-3-{1-[(1-[(p-chlorophenyl)carbamoyl]-2-methylpropyl}-2,5-dioxo-4-imidazolidinylurea (200 mg) in 0.4 ml of 1M hydrobromic acid in acetic acid is held at room temperature for 3 days, treated with methanol, held at ambient temperatures for an additional 30 minutes, treated with ethylacetate, washed sequentially with dilute aqueous hydrochloric acid, and aqueous sodium bicarbonate, and concentrated in vacuo to give a yellow oil residue. The oil is purified by flash chromatography on silica gel (hexane/ethyl,acetate-70/30) to give the title product as a white solid (120 mg, mp, 160°–164° C.), identified by HNMR, CIMS and IR analyses.

EXAMPLE 7

EVALUATION OF FUNGICIDAL ACTIVITY OF TEST COMPOUND

The test compound is dissolved in acetone, diluted to the desired concentration with water and surfactant and sprayed onto the test plants. After drying, the test plants are treated with fungal inoculum. When disease symptom development is optimal plants are rated for disease control. Inoculated untreated plants, solvent/surfactant treated plants and plants treated with a reference standard are used for comparison.

| | TEST ORGANISMS | |
|---|---|---|
| Header | Common Name | Scientific Name |
| GDM | Grape downy mildew | *Plasmopara viticola* |
| TLB | Tomato late blight | *Phytophthora infestans* |

TABLE I

| EXAMPLE NOS. | TARGET | RATE (PPM) | % CONTROL |
|---|---|---|---|
| 6 | GDM | 200 | 100 |
| | | 50 | 98 |
| | | 12.5 | 70 |
| 6 | TLB | 200 | 100 |
| | | 50 | 90 |
| | | 12.5 | 70 |

We claim:
1. A compound having the formula

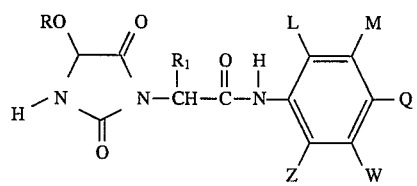

wherein

R is hydrogen, $C_1$–$C_8$alkyl, $C_1$–$C_4$haloalkyl or benzyl;

$R_1$ is hydrogen, $C_1$–$C_8$alkyl, $C_3$–$C_6$cycloalkyl, phenyl, benzyl or phenethyl;

L, M, Q, W and Z are each independently hydrogen, $C_1$–$C_6$ alkyl, $C_1$–$C_4$alkoxyalkyl, $C_1$–$C_6$haloalkyl, $C_1$–$C_4$ alkoxy, halogen, $NO_2$, CN, $CO_2R_3$, phenyl or phenoxy with the proviso that no more than 3 of L, M, Q, W and Z may be phenyl or phenoxy;

$R_3$ is $C_1$–$C_4$ alkyl; and when $R_1$ is a substituent other than hydrogen, the optical isomers thereof.

2. The compound according to claim 1 wherein

R is $C_1$–$C_8$ alkyl, $C_1$–$C_4$haloalkyl or phenyl;

$R_1$ is hydrogen, $C_1$–$C_8$ alkyl, benzyl or phenethyl; and

L, M, Q, W and Z are each independently hydrogen, $C_1$–$C_6$ alkyl, $C_1$–$C_4$ alkoxy, halogen, phenyl or phenoxy with the proviso that no more than 3 of L, M, Q, W and Z may be phenyl or phenoxy.

3. The compound according to claim 2 wherein R is $C_1$–$C_8$alkyl; $R_1$ is hydrogen, $C_1$–$C_6$alkyl, benzyl or phenethyl; and L, M, Q, W and Z are each independently hydrogen, $C_1$–$C_6$alkyl, $C_1$–$C_4$alkoxy, or halogen.

4. The compound according to claim 3 4'-chloro-α-(isopropyl-2,5-dioxo-4-methoxy-1-imidazolidine)acetanilide.

5. A method for the control of a phytopathogenic fungus which comprises contacting said fungus with a fungicidally effective amount of a compound of formula I

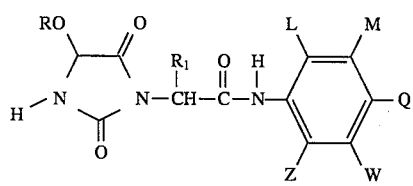

wherein

R is hydrogen, $C_1$–$C_8$alkyl, $C_1$–$C_4$haloalkyl, or benzyl;

$R_1$ is hydrogen, $C_1$–$C_8$alkyl, $C_3$–$C_6$cycloalkyl, phenyl, benzyl or phenethyl;

L, M, Q, W and Z are each independently hydrogen, $C_1$–$C_6$ alkyl, $C_1$–$C_4$alkoxyalkyl, $C_1$–$C_6$haloalkyl, $C_1$–$C_4$ alkoxy, halogen, $NO_2$, CN, $CO_2R_3$, phenyl or phenoxy with the proviso that no more than 3 of L, M, Q W and Z may be phenyl or phenoxy;

$R_3$ is $C_1$–$C_4$ alkyl; and when $R_1$ is a substituent other than hydrogen, the optical isomers thereof.

6. The method according to claim 5 wherein the phytopathogenic fungus is a member of the oomycota.

7. The method according to claim 6 wherein the phytopathogenic fungus is *Plasmopara viticola* or *Phytophthora infestans*.

8. The method according to claim 5 wherein the compound is applied as a dilute spray at a concentration of about 20 ppm to 1,000 ppm.

9. The method according to claim 5 wherein

R is $C_1$–$C_8$alkyl, C1–C4haloalkyl, or phenyl;

$R_1$ is hydrogen, $C_1$–$C_8$ alkyl, benzyl or phenethyl; and

L, M, Q, W and Z are each independently hydrogen, $C_1$–$C_4$ alkoxy, halogen, phenyl or phenoxy with the proviso than no more than 3 of L, M, Q, W, and Z may be phenyl or phenoxy.

10. The method according to claim 9 wherein R is $C_1$–$C_8$alkyl; $R_1$ is hydrogen, $C_1$–$C_6$alkyl, benzyl or phenethyl; and L, M, Q, W and Z are each independently hydrogen, $C_1$–$C_6$alkyl, $C_1$–$C_4$alkoxy, or halogen.

11. The method according to claim 10 wherein the compound is 4'-chloro-α-(isopropyl-2,5-dioxo-4-methoxy-1-imidazolidine)acetanilide.

12. A method for the protection of a plant from disease caused by a phytopathogenic fungus which comprises applying to the foliage of the plant, the seed or tuber of the plant, or the soil or water in which the plant is growing or is to be grown, a fungicidally effective amount of a compound of formula I wherein R, $R_1$, L, M, Q, W and Z are as described in claim 5.

13. The method according to claim 12 wherein the disease is mildew or blight.

14. The method according to claim 13 wherein the disease is grape downey mildew or tomato late blight.

15. The method according to claim 12 wherein R is $C_1$–$C_8$alkyl; $R_1$ is hydrogen, $C_1$–$C_6$alkyl, benzyl or phenethyl; and L, M, Q, W and Z are each independently hydrogen, $C_1$–$C_6$alkyl, $C_1$–$C_4$alkoxy or halogen.

16. The method according to claim 15 wherein the formula I compound is 4'-chloro-α-(isopropyl-2,5-dioxo-4-methoxy-1-imidazolidine)acetanilide.

17. A fungicidal composition which comprises an agriculturally acceptable solid or liquid diluent and a fungicidally effective amount of a compound of formula I.

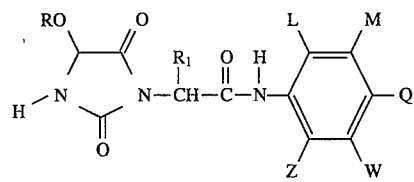

wherein

R is hydrogen, $C_1$–$C_8$alkyl, $C_1$–$C_4$haloalkyl or benzyl;

$R_1$ is hydrogen, $C_1$–$C_8$alkyl, $C_3$–$C_6$cycloalkyl, phenyl, benzyl or phenethyl;

L, M, Q, W and Z are each independently hydrogen, $C_1$–$C_6$ alkyl, $C_1$–$C_4$alkoxyalkyl, $C_1$–$C_6$haloalkyl, $C_1$–$C_4$alkoxy, halogen, $NO_2$, CN, $CO_2R_3$, phenyl or phenoxy with the proviso that no more than 3 of L, M, Q, W and Z may be phenyl or phenoxy;

$R_3$ is $C_1$–$C_4$ alkyl; and when $R_1$ is a substituent other than hydrogen, the optical isomers thereof.

18. The composition according to claim 17 wherein

R is $C_1$–$C_8$alkyl, $C_1$–$C_4$haloalkyl or phenyl;

$R_1$ is hydrogen, $C_1$–$C_8$alkyl, benzyl or phenethyl; and

L, M, Q, W and Z are each independently hydrogen, $C_1$–$C_6$ alkyl, $C_1$–$C_4$alkoxy, halogen, phenyl or phenoxy with the proviso that no more than 3 of L, M, Q,W and Z may be phenyl or phenoxy.

19. The composition according to claim 18 R is $C_1$–$C_8$alkyl; $R_1$ is hydrogen, $C_1$–$C_6$alkyl, benzyl or phenethyl; and L, M, Q, W and Z are each independently hydrogen, $C_1$–$C_6$alkyl, $C_1$–$C_4$alkoxy, or halogen.

20. The composition according to claim 19 wherein the compound is 4'-chloro-α-(isopropyl-2,5-dioxo- 4-methoxy-1-imidazolidine)acetanilide.

* * * * *